US006573217B2

(12) United States Patent
Bickers et al.

(10) Patent No.: US 6,573,217 B2
(45) Date of Patent: Jun. 3, 2003

(54) HERBICIDAL COMPOSITIONS

(75) Inventors: Udo Bickers, Wietmarschen (DE); Hermann Bieringer, Eppstein (DE); Gerhard Frisch, Wehrheim (DE); Erwin Hacker, Hochheim (DE); Hans Philipp Huff, Eppstein (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/911,032

(22) Filed: Jul. 23, 2001

(65) Prior Publication Data

US 2002/0072474 A1 Jun. 13, 2002

(30) Foreign Application Priority Data

Jul. 25, 2000 (DE) .......................................... 100 36 003

(51) Int. Cl.$^7$ ........................ A01N 25/30; A01N 37/28; A01N 47/34
(52) U.S. Cl. ....................... 504/212; 504/214; 504/333; 504/363
(58) Field of Search ................................. 504/214, 363, 504/212, 333

(56) References Cited

U.S. PATENT DOCUMENTS 6,010,979 A * 1/2000 Osborn et al. .............. 504/206

\* cited by examiner

*Primary Examiner*—S. Mark Clardy
(74) *Attorney, Agent, or Firm*—Frommer Lawrence & Haug LLP

(57) ABSTRACT

The present invention relates to a herbicidal composition comprising
d) one or more herbicidal active substances from the group of the grass-controlling sulfonamides,
e) one or more silicone surfactants, and
f) one or more humectants.

The composition according to the invention is outstandingly suitable for controlling a variety of harmful plants.

11 Claims, No Drawings

HERBICIDAL COMPOSITIONS

The invention lies in the technical field of the crop protection products, in particular active substance/silicone surfactant/humectant combinations.

To control undesired harmful plants, a multiplicity of herbicides is available to the user, which can be employed as a function of the biological properties of the herbicides, the species of harmful plants to be controlled and the crop plant species. In this context, the herbicidal active substances are formulated in such a way that their application is as optimal as possible and that they have high activity. A variety of formulation auxiliaries such as wetters, dispersants, emulsifiers, antifoams, as solvents or fillers are employed for this purpose.

However, the reliability and the level of the control of the harmful plants vary as a function of environmental factors such as temperature, atmospheric humidity, soil moisture, light incidence, precipitation or soil type, which can lead to follow-up treatments in the event of poor activity or to the damage of useful plants in the case of unduly high rates of application.

A more reliable activity also has ecological advantages. To avoid poor activity, the user frequently increases the amount of active substance to be applied. However, the disadvantage of this procedure is that the active substances' potential to affect soil fauna, to leach from the soil or to enter surface waters increases.

The effect of humectants on a variety of pesticides is described in Adjuvants for Agrochemicals, CRC Press, Inc. (1992), pp. 261–271. WO 89/02570 discloses that humectants in conjunction with silicone surfactants can increase the activity of herbicides.

It was an object of the present invention to provide a herbicidal composition with improved level of action and improved reliability of action. This object is achieved by a herbicidal composition comprising specific sulfonamides in combination with silicone surfactants and humectants.

The present invention thus relates to a herbicidal composition comprising
a) one or more herbicidal active substances from the group of the grass-controlling sulfonamides,
b) one or more silicone surfactants, and
c) one or more humectants.

The grass-controlling sulfonamides which are present in the herbicidal composition according to the invention as component a) are understood to be sulfonamides which inhibit the growth of monocotyledonous harmful plants in a sustained manner. In particular, they encompass sulfonamides which are recommended by the manufacturer for use against monocotyledonous harmful plants, for example in the product brochures in question or in Pesticide Manual, 12th edition (2000), British Crop Protection Council.

Examples of especially suitable active substances from the group of the grass-controlling sulfonamides are grass-controlling sulfonylureas such as flucarbazone (MKH 6561), procarbazone (MKH 6562), sulfosulfuron, rimsulfuron, nicosulfuron, flupyrsulfuron, iodosulfuron-methyl, foramsulfuron (Agrow No. 338, PJB Publications Ltd. 1999, page 26) and mesosulfuron-methyl and/or their salts (Agrow No. 347, PJB Publications Ltd. 2000, page 22).

Very especially preferred are sulfonylureas of the formula (I) and/or their salts

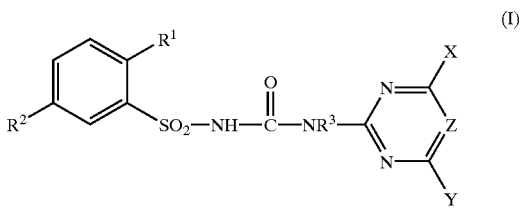

in which $R^1$ is CO—$R^a$, in which $R^a$ is OH, $C_1$–$C_4$-alkoxy or $NR^bR^c$, in which $R^b$ and $R^c$ independently of one another are identical or different and are H or $C_1$–$C_4$-alkyl, $R^2$ is halogen or $(A)_n$—$NR^dR^e$ in which n is zero or 1, A is a group CR'R" in which R' and R" independently of one another are identical or different and are H or $C_1$–$C_4$-alkyl, $R^d$ is H or $C_1$–$C_4$-alkyl and $R^e$ is an acyl radical, $R^3$ is H or $C_1$–$C_4$-alkyl, X and Y independently of one another are identical or different and are $C_1$–$C_6$-alkyl, $C_1$–$C_6$-alkoxy or $C_1$–$C_6$-alkylthio, where each of the three abovementioned radicals is unsubstituted or substituted by one or more radicals selected from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, preferably $C_1$–$C_4$-alkyl or $C_1$–$C_4$-alkoxy, and Z is CH or N.

Examples of sulfonylureas of the formula (I) and/or their salts are mesosulfuron-methyl, mesosulfuron-methyl-sodium, iodosulfuron-methyl, iodosulfuron-methyl-sodium, foramsulfuron and foramsulfuron-sodium.

Examples of suitable salts of the sulfonamides a) such as sulfonylureas are compounds in which the hydrogen of the —$SO_2$—NH-group is replaced by an agriculturally suitable cation. Examples of these salts are metal salts, in particular alkali metal salts or alkaline earth metal salts, in particular sodium salts and potassium salts, or else ammonium salts or salts with organic amines. Equally, salt formation can be effected by an addition reaction of an acid with basic groups such as, for example, amino and alkylamino. Acids which are suitable for this purpose are strong inorganic and organic acids, for example HCl, HBr, $H_2SO_4$ or $HNO_3$.

The silicone surfactants present in the herbicidal composition according to the invention as component b) are understood as surfactants with at least one silicon atom, preferably 2 to 2000 silicon atoms.

The silicone surfactants b) which are present in the herbicidal compositions according to the invention are, for example, polyalkylene oxide-modified dimethylpolysiloxane copolymers which are commercially available for example under the trademark Silwet by Witco/Osi Corp., which was Union Carbide Corporation (USA). They are surface-active materials with discrete hydrophilic and hydrophobic segments. They have the following formula (I)

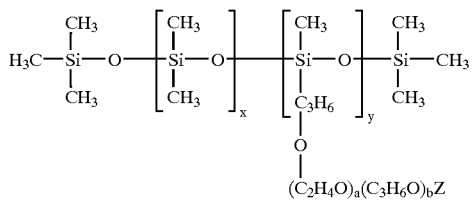

(I)

in which a is an integer of 3–24, b an integer of 0–15, x an integer of 0–3 and y an integer of 1–5, and Z is hydrogen, $C_1$–$C_3$-alkyl or an acyl group having 2 to 4 carbon atoms.

The Silwet silicone surfactants also include the products described in the Union Carbide brochure entitled "Silicones For the Agricultural Industry" SUI-356, 6/84, 5M and in "Surface Active Copolymers", SUI-394A, 7185–5M, also from Union Carbide. Both brochures are incorporated in their entirety into the present description by reference.

Further suitable silicone surfactants which can be used for the purposes of the present invention are, for example SF-1188 (General Electric Company, Silicone Products Division, Rubber & Fluid Products Department, Waterford, N.Y. 12188), Silwet L-7607, the silicone glycols Q2-5309, Q2-5152, Q2-5852 and Q2-5853 by Dow Corning Corporation, Midland, Mich., mixtures of these, and similar products. Silicone surfactants of the formula (I) are described in particular in U.S. Pat. No. 3,299,112, which is incorporated in its entirety into the present description by reference. An especially preferred silicone surfactant has the formula $Me_3SiO[MeO(C_2H_4O)_7C_3H_6SiMeO]SiMe_3$ in which Me=methyl.

Other suitable silicone surfactants b) are silicone glycols, for example of the formula (II):

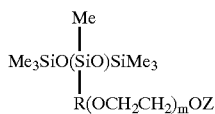

(II)

where Me hereinbelow denotes a methyl radical, R a divalent alkylene group having 2 to 6 carbon atoms, such as ethylene, trimethylene, tetramethylene or hexamethylene, preferably trimethylene, m is an integer of 3–24 and Z is hydrogen, a $C_1$–$C_3$-alkyl radical or an acyl group having 2 to 4 carbon atoms, preferably an acetoxy group.

The above-described silicone glycols are known in the art and can be prepared for example by coupling the corresponding glycol, which has a terminal allyl group, to a bis-siloxane structure which has a hydrogen atom at the central silicon atom, where the bis-siloxane structure can be represented as follows (in which Me=methyl):

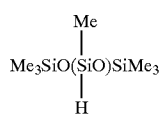

(III)

In general, this coupling reaction is carried out in the presence of a platinum catalyst. It is known in the art that not all the glycol with the terminal allyl group is reacted in such coupling reactions and remains in the silicone glycol end product as contaminant. The present invention also encompasses herbicidal compositions with such contaminants.

Silicone glycol/silicone alkane terpolymers are also suitable as silicone surfactants b) which are present in accordance with the invention. These compounds can be represented for example by the following formula (IV):

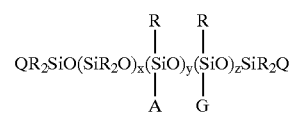

(IV)

in which R are $C_1$–$C_6$-alkyl radicals which are identical or different from each other, A is a $C_7$–$C_{30}$-alkyl radical, G is a glycol unit of the formula —$R'(OCH_2CH_2)_mOZ$, where R' is a divalent $C_1$–$C_6$-alkylene group and Z is hydrogen, a $C_1$–$C_3$-alkyl radical or a $C_2$–$C_4$-acyl group, and m is an integer of from 8–100; Q are identical or different from each other and selected from among the meanings given for the abovementioned alkyl radical A, the abovementioned glycol unit G and the abovementioned alkyl radical R; x is an integer of from 0 to 100, y is an integer of from 0 to 25 and z is an integer of from 0 to 50, and the total is $x+y+z \geq 1$.

An especially preferred silicone glycol/silicone alkane terpolymer of the formula (IV) which is suitable as silicone surfactant for the present invention has the following formula (V):

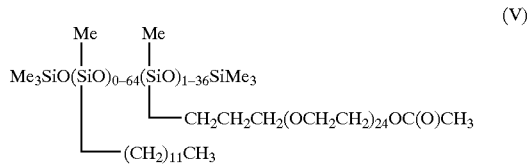

(V)

in which Me is a methyl radical.

The above-described silicone glycol/silicone alkane terpolymer can be prepared by methods well known in the art. For example, the corresponding glycol which has a terminal allyl group can be coupled with an α-alkene to given an SiH-functional siloxane which has the following formula (VI):

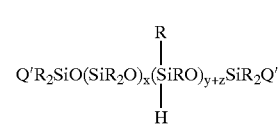

(VI)

in which R, x, y and z have the meanings given above in formula (IV) and Q' are identical or different from each other and are hydrogen or have the meanings given for R.

To prepare the above-described, especially preferred silicone glycol/silicone alkane terpolymer, 0.77 mol of α-dodecene and 1.90 mol of a glycol with terminal allyl group of the formula $CH_2=CHCH_2(OCH_2CH_2)_{24}OC(O)CH_3$ are reacted with 1 mol of an SiH-functional siloxane with the following formula (VII)

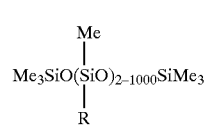

(VII)

in which R=H, $C_1$–$C_6$-alkyl, $C_1$–$C_6$-hydroxyalkyl to yield 1 mol of the terpolymer. Coupling is effected in the presence of a platinum catalyst at temperatures in the range from approx. 20° C. to approx. 150° C. The reaction is preferably carried out in a solvent such as toluene or isopropanol.

Furthermore preferred silicone surfactants b) are polyalkylsiloxanes, for example of the type of the compounds of the formula (VII) such as the Tegopren® brands by Goldschmidt and the E® and SE® brands by Wacker, the Rhodorsil® and Silcolapse® brands by Rhodia and the Bevaloid® brands by Dow Corning.

A humectant is understood as meaning, for the purposes of the present invention, a compound which is capable of physically absorbing water and/or storing water. Preferred humectants are, for example, hygroscopic compounds.

Examples of substances which may be present in the herbicidal compositions according to the invention as humectant c) are the following: $MgSO_4$, polyhydric alcohols such as ethylene glycol, propylene glycol, butanediol, glycerol and pentaerythritol, and their ethers and esters, for example ethylene, glycol ethers, propylene glycol ethers or glycerol esters; polyalkylene glycols such as polyethylene glycols (preferably with a molecular weight of 500–60000), polypropylene glycols (preferably with a molecular weight of 600–75000) and ethylene oxide (EO)/propylene oxide (PO) copolymers, for example with EO-PO-, EO-PO-EO- or PO-EO-PO units; sugars such as hexoses, pentoses, molasses, alkylpolysaccharides and xanthans, for example the Maltitol® brands by Salim Oleo Chemicals such as Maltitol® 75; gelatin; cellulose derivatives such as water-soluble lignosulfonates or hydroxycelluloses; citric acid and citric acid derivatives such as citric acid salts, for example alkali metal, alkaline earth metal or ammonium citrates, such as sodium citrate; lactic acid and lactic acid derivatives such as lactic acid salts, for example alkali metal, alkaline earth metal or ammonium lactates, such as sodium lactate, for example in the form of their racemates (DL) or of the individual optical isomers, for example sodium D-lactate and sodium L-lactate; tartaric acid and tartaric acid derivatives such as tartaric acid salts, for example alkali metal, alkaline earth metal or ammonium tartrates such as sodium tartrate, for example in the form of their racemates (uvic acid) or of the individual optical isomers, for example sodium (+)-tartrate and sodium (−)-tartrate; aspartic acid and aspartic acid derivatives such as aspartic acid salts, for example alkali metal, alkaline earth metal or ammonium aspartates such as sodium aspartate, for example in the form of their racemates (DL) or of the individual optical isomers, for example sodium D-aspartate and sodium L-aspartate; succinates such as the Triton® brands by Rohm and Haas; polyvinyl compounds such as modified polyvinylpyrrolidone such as the Luviskol® brands by BASF and the Agrimer® brands by ISP or the derivatized polyvinyl acetates such as the Mowilith® brands by Clariant or the polyvinyl butyrates such as the Lutonal® brands by BASF, the Vinnapas® and the Pioloform® brands by Wacker or the modified polyvinyl alcohols such as the Mowiol® brands by Clariant. Preferred humectants are polyhydric alcohols such as ethylene glycol or propylene glycol and lactic acid and lactic acid derivatives such as lactic acid salts, for example alkali metal, alkaline earth metal or ammonium lactates such as sodium lactate, for example in the form of their racemates (DL) or of the individual optical isomers, for example sodium D-lactate and sodium L-lactate.

The herbicidal compositions according to the invention conventionally comprise
a) 0.0001 to 99% by weight, preferably 0.1 to 95% by weight, of one or more grass-controlling sulfonamides,
b) 0.1 to 97% by weight of one or more silicone surfactants, and
c) 0.1 to 90% by weight of one or more humectants.

The herbicidal compositions according to the invention have an outstanding herbicidal activity. The improved control of the harmful plants by the herbicidal compositions according to the invention makes it possible to reduce the application rate and/or to increase the safety margin. Both make sense both from the economical and the ecological angle.

In a preferred embodiment, herbicidal compositions according to the invention are characterized by a synergistically active content of a combination of the herbicides a) with surfactants b) and humectants c). In this context, it must be emphasized in particular that, as a rule, the herbicidal compositions of the invention have an inherent synergistic action, even in combinations with application rates or weight ratios of a):b):c) where synergism cannot be detected readily in each individual case, for example because the individual compounds are usually employed in very different application rates in the combination or else because even the individual compounds alone effect very good control of the harmful plants.

The herbicidal compositions according to the invention are prepared by customary processes, for example grinding, mixing, dissolving or dispersing individual components.

The components a), b) and c) of the herbicidal compositions according to the invention may be present together in a readymix which can then be applied in the customary fashion, for example in the form of a spray mixture, or they can be formulated separately and applied for example by the tank mix method or in succession. When the components are formulated separately, components a), b) and c) can be formulated for example in each case individually, or else components a) and b), a) and c) or b) and c) can be formulated jointly and the third component in question is formulated separately.

The herbicidal compositions according to the invention can be formulated in various ways, depending on the prevailing biological and/or chemical-physical parameters. The following are examples of suitable formulation possibilities: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusts (DP), seed-dressing materials, granules for spreading and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Engineering], Volume 7, C. HauserVerlag Munich, $4^{th}$ Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and other additives, are also known and are described, for example, in Watkins, "Handbook of Insecticide Dust Diluents and Carriers", 2nd Ed., Darland Books, Caldwell N. J., H. V. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N. J.; Sisley and Wood, "Encyclopedia of Surface Active Agents", Chem. Publ. Co. Inc., N.Y. 1964; Schonfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4$^{th}$ Ed. 1986.

Based on these formulations, it is also possible to prepare combinations with other agrochemical active substances such as insecticides, acaricides, herbicides, fungicides, safeners, fertilizers and/or growth regulators, for example in the form of a readymix or a tank mix.

Wettable powders are products which are uniformly dispersible in water and which, besides the herbicide a) and/or surfactant b) and/or humectant c), also comprise diluents or inert materials and, if appropriate further ionic and/or non-ionic surfactants (wetters, dispersants) other than the silicone surfactants b), for example polyoxyethylated alkylphenols, polyoxethylated fatty alcohols, polyoxethylated fatty amines, fatty alcohol polyglycol ether sulfates, alkanesulfonates, alkylbenzenesulfonates, sodium lignosulfonates, sodium 2,2'-dinaphthylmethane-6,6'-disulfonate, sodium dibutyinaphthalene sulfonate or else sodium oleoylmethyltauride. To prepare the wettable powders, the herbicides a) and/or surfactants b) and/or humectants c) are ground finely, for example in customary apparatuses such as hammer mills, blower mills and air-jet mills, and mixed with the formulation auxiliaries, either simultaneously or subsequently.

Emulsifiable concentrates are prepared by dissolving herbicide a) and/or surfactant b) and/or humectant c) in an organic solvent, for example butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which may be used are: calcium salts of alkylarylsulfonic acid, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters, or polyoxyethylene sorbitan esters such as, for example, polyoxyethylene sorbitan fatty acid esters.

Dusts are obtained by grinding herbicide a) and/or surfactant b) and/or humectant c) with finely divided solid materials, for example talc, natural clays such as kaolin, bentonite and pyrophyllite, or diatomaceous earth.

Suspension concentrates can be water- or oil-based. They can be prepared, for example by wet grinding by means of commercially available bead mills and, if appropriate, with addition of surfactants other than the silicone surfactants b) as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants other than the silicone surfactants b) as have already been mentioned for example above in the case of the other formulation types.

Granules can be prepared either by spraying the herbicide a) and/or surfactant b) and/or humectant c) onto adsorptive, granulated inert material or by applying active ingredient concentrates to the surface of carriers such as sand, kaolinites or of granulated inert material with the aid of adhesives, for example polyvinyl alcohol, sodium polyacrylate or else mineral oils. Suitable herbicides a) and/or surfactants b) and/or humectants c) may also be granulated in the manner conventionally used for the production of fertilizer granules, if desired in a mixture with fertilizers. As a rule, water-dispersible granules are prepared by conventional processes such as spray drying, fluidized-bed granulation, disk granulation, mixing with high-speed mixers and extrusion without solid inert material. Regarding the production of disk granules, fluidized-bed granules, extruder granules and spray granules, see, for example, the methods in "Spray-Drying Handbook" 3rd Ed. 1979, G. Goodwin Ltd., London; J. E. Browning, "Agglomeration", Chemical and Engineering 1967, page 147 et seq; "Perry's Chemical Engineer's Handbook", 5th Ed., McGraw-Hill, New York 1973, pp. 8–57.

For further details on the formulation of crop protection products, see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

In addition, the abovementioned active ingredient formulations may comprise, if appropriate, the additives such as adhesives, wetters, dispersants, emulsifiers, penetrants, preservatives, antifreeze agents, solvents, fillers, carriers, colorants, antifoams, evaporation inhibitors, pH regulators or viscosity regulators which are customary in each case.

The herbicidal compositions according to the invention can be used pre- or post-emergence, for example by spraying. The product input required for weed control can be reduced substantially by employing the herbicidal compositions according to the invention.

As a rule, the herbicides a) to be used in accordance with the invention are applied together with the surfactant(s) b) and humectant(s) c) or in succession, preferably in the form of a spray mixture comprising the herbicides a), the surfactants b) and the humectants c) in effective amounts and, if appropriate, further customary auxiliaries. The spray mixture is preferably prepared on the basis of water and/or an oil, for example a high-boiling hydrocarbon such as kerosene or paraffin. The herbicidal compositions according to the invention can be formulated as a tank mix or a readymix.

The active ingredient concentration in wettable powders is, for example, approximately 10 to 90% by weight, the remainder to 100% by weight being composed of customary formulation constituents. In the case of emulsifiable concentrates, the active ingredient concentration may amount to approximately I to 90%, preferably 5 to 80% by weight. Formulations in the form of dusts comprise 1 to 30% by weight of active ingredient, preferably in most cases 5 to 20% by weight of active ingredient, sprayable solutions contain approximately 0.05 to 80%, preferably 2 to 50% by weight of active ingredient. In the case of water-dispersible granules, the active ingredient content depends partly on whether the active compound is present in liquid or solid form and on which granulation auxiliaries, fillers and the like are being used. The active ingredient content amounts to, for example, between 1 and 95% by weight, preferably to between 10 and 80% by weight in the case of the water-dispersible granules.

The amount of surfactant b) in concentrated formulations can naturally not be increased at will without adversely affecting the stability of the formulation. In the concentrated formulations, the weight ratio herbicide a):surfactant b) is generally 1000:1 to 1:10000, preferably 200:1 to 1:200; the weight ratio herbicide a):humectant c) is generally from 1000:1 to 1:10000, preferably 200:1 to 1:200; and the weight ratio of surfactant b):humectant c) is generally 1000:1 to 1:1000, preferably 200:1 to 1:200.

Upon application, the weight ratio herbicide a): surfactant b) is generally in the range of from 1000:1 to 1:100000, in particular 200:1 to 1:1000, depending on the efficacy of the herbicide in question. The weight ratio herbicide a):humectant c) is upon application in general in the range from 1000:1 to 1:100000, in particular 200:1 to 1:200 depending on the efficacy of the herbicide in question. The weight ratio surfactant b):humectant c) upon application is generally in the range of from 1000:1 to 1:1000, preferably 200:1 to 1:200.

Upon application, the concentration of herbicide a) is generally 0.0001 to 20% by weight, preferably 0.01 to 3% by weight, in the composition applied, for example the spray mixture, at an application rate of 5 to 4000 I/ha, preferably 100 to 600 I/ha. In general, the concentration of surfactant b) is 0.001 to 5% by weight, preferably 0.1 to 2.0% by weight, in particular 0.1 to 0.5% by weight, in the composition applied, for example the spray mixture, at an application rate of 5 to 4000 I/ha, preferably 100 to 600 I/ha. In general, the concentration of humectant c) is 0.001 to 20% by weight, preferably 0.01 to 5% by weight, of humectant c) in the composition applied, for example the spray mixture, at an application rate of 5 to 4000 I/ha, preferably 100 to 600 I/ha.

In addition to the surfactants b), the herbicidal compositions according to the invention can also comprise other ionic and nonionic surfactants, such as aromatic-based surfactants, for example surface-active benzenes or phenols which are substituted by one or more alkyl groups and have subsequently been derivatized, or nonaromatic-based surfactants, for example heterocycle-, olefin-, aliphatic- or cycloaliphatic-based surfactants, for example surface-active pyridine, pyrimidine, triazine, pyrrole, pyrrolidine, furan, thiophene, benzoxazole, benzothiazole and triazole compounds which are substituted by one or more alkyl groups and have subsequently been derivatized.

Examples of aromatic surfactants are:
1) phenols, phenyl ($C_1$–$C_4$)alkyl ethers or (poly)alkoxylated phenols [=phenol (poly)alkylene glycol ethers], for example having 1 to 50 alkyleneoxy units in the (poly)alkyleneoxy moiety, where the alkylene moiety has preferably in each case 1 to 4 carbon atoms, preferably phenol which has been reacted with 3 to 10 mol of alkylene oxide,
2) (poly)alkylphenols or (poly)alkylphenol alkoxylates [polyalkylphenol (poly)alkylene glycol ethers], for example having 1 to 12 carbon atoms per alkyl radical and 1 to 150 alkyleneoxy units in the polyalkyleneoxy moiety, preferably triisobutylphenol or tri-n-butylphenol which has been reacted with 1 to 50 mol of ethylene oxide,
3) polyarylphenols or polyarylphenol alkoxylates [=polyarylphenol (poly)alkylene glycol ethers], for example tristyrylphenol polyalkylene glycol ethers with 1 to 150 alkyleneoxy units in the polyalkyleneoxy moiety, preferably tristyrylphenol which has been reacted with 1 to 50 mol of ethylene oxide,
4) compounds which formally constitute the reaction products of the molecules described under 1) to 3) with sulfuric acid or phosphoric acid and their salts which have been neutralized with suitable bases, for example the acid phosphoric ester of the triethoxylated phenol, the acid phosphoric ester of a nonylphenol which has been reacted with 9 mol of ethylene oxide, and the triethanolamine-neutralized phosphoric acid ester of the reaction product of 20 mol of ethylene oxide and 1 mol of tristyrylphenol, and
5) acid (poly)alkyl- and (poly)arylbenzenesulfonates which have been neutralized with suitable bases, for example having 1 to 12 carbon atoms per alkyl radical, or having up to 3 styrene units in the polyaryl radical, preferably (linear) dodecylbenzenesulfonic acid and its oil-soluble salts such as, for example, the isopropylammonium salt of dodecylbenzenesulfonic acid.

In the case of the alkyleneoxy units, ethyleneoxy, propyleneoxy and butyleneoxy units, in particular ethyleneoxy units, are preferred. Preferred surfactants from the group of the aromatic-based surfactants are, in particular, for example phenol which has been reacted with 4 to 10 mol of ethylene oxide, commercially available for example in the form of the Agrisol® brands (Akcros), triisobutylphenol which has been reacted with 4 to 50 mol of ethylene oxide, commercially available for example in the form of the Sapogenat® brands (Clariant), nonylphenol which has been reacted with 4 to 50 mol of ethylene oxide, for example commercially available in the form of the Arkopal® brands (Clariant), tristyrylphenol which has been reacted with 4 to 150 mol of ethylene oxide, for example Soprophor®CY/8 (Rhodia), and acid (linear) dodecylbenzenesulfonate, for example commercially available in the form of the Marion® brands (Hüls).

Examples of nonaromatic surfactants are given hereinbelow, where EO=ethylene oxide units, PO=propylene oxide units and BO=butylene oxide units:

α.1) fatty alcohols having 10–24 carbon atoms with 0–60 EO and/or 0–20 PO and/or 0–15 BO in any desired sequence. The terminal hydroxyl groups of these compounds can be terminally capped by an alkyl, cycloalkyl or acyl radical having 1–24 carbon atoms. Examples of such compounds are: Genapol®C,L,O,T,UD,UDD,X brands by Clariant, Plurafac® and Lutensol®A, AT,ON, TO brands by BASF, Marlipal®24 and O13 brands by Condea, Dehypon® brands by Henkel, Ethylan® brands by Akzo-Nobel such as Ethylan CD 120 or Synperonic® brands by Unichem, for example Synperonic®A7.

α.2) Anionic derivatives of the products described under α.1) in the form of ether carboxylates, sulfonates, sulfates and phosphates and their inorganic salts (for example alkali metal salts and alkaline earth metal salts) and organic salts (for example based on amine or alkanolamine) such as Genapol®LRO, Sandopan® brands, Hostaphat/Hordaphos® brands by Clariant.

Copolymers composed of EO, PO and/or BO units such as, for example, block copolymers such as the Pluronic® brands by BASF and the Synperonic® brands by Uniquema with a molecular weight of 400 to $10^8$.

Alkylene oxide adducts of $C_1$–$C_9$ alcohols such as Atlox®5000 by Uniquema or Hoe® S3510 by Clariant.

Anionic derivatives of the products described under α.3) and α.4) in the form of ether carboxylates, sulfonates, sulfates and phosphates and their inorganic salts (for example alkali metal salts and alkaline earth metal salts) and organic salts (for example based on amine or alkanolamine).

α.3) Fatty acid and triglyceride alkoxylates such as the Serdox®NOG brands by Condea or the Emulsogen® brands by Clariant, salts of aliphatic, cycloaliphatic and olefinic carboxylic acids and polycarboxylic acids, and alpha-sulfofatty acid esters as available from Henkel.

α.4) Fatty acid amide alkoxylates such as the Comperlan® brands by Henkel or the Amam® brands by Rhodia.

Alkylene oxide adducts of alkyne diols such as the Surfynol® brands by Air Products. Sugar derivatives such as amino and amido sugars from Clariant, glucitols from Clariant, alkyl polyglycosides in the form of the APG® brands by Henkel or such as sorbitan esters in the form of the Span® or Tween® brands by Uniquema or cyclodextrin esters or ethers from Wacker.

α.5) Surface-active cellulose and algin, pectin and guar derivatives such as the Tylose® brands by Clariant, the Manutexe brands by Kelco and guar derivatives from Cesalpina.

Alkylene oxide adducts on a polyol base such as Polyglykol® brands by Clariant. Surface-active polyglycerides and their derivatives from Clariant.

α.6) Sulfosuccinates, alkanesulfonates, paraffin- and olefinsulfonates such as Netzer IS®, Hoe®S1728, Hostapur®OS, Hostapur®SAS by Clariant, Triton®GR7ME and GR5 by Union Carbide, Empimin® brands by Albright and Wilson, Marlon®-PS65 by Condea.

α.7) Sulfosuccinates such as the Aerosol® brands by Cytec or the Empimin® brands by Albright and Wilson.

α.8) Alkylene oxide adducts of fatty amines, quaternary ammonium compounds with 8 to 22 carbon atoms ($C_8$–$C_{22}$) such as, for example, the Genamin®C,L,O,T brands by Clariant.

α.9) Surface-active, zwitterionic compounds such as taurides, betaines and sulfobetaines in the form of Tegotain® brands by Goldschmidt, Hostapon®T and Arkopon®T brands by Clariant.

α.10) Per- or polyfluorinated surface-active compounds such as Fluowete brands by Clariant, the Bayowet® brands by Bayer, the Zonyl® brands by DuPont, and products of this type from Daikin and Asahi Glass.

α.11) Surface-active sulfonamides, for example from Bayer.

α.12) Surface-active polyacrylic and -methacrylic derivatives such as the Sokalan® brands by BASF.

α.13) Surface-active polyamides such as modified gelatin or derivatized polyaspartic acid from Bayer and their derivatives.

α.14) Surface-active polymers based on maleic anhydride and/or reaction products of maleic anhydride, and copolymers comprising maleic anhydride and/or reaction products of maleic anhydride, such as the Agrimer®VEMA brands by ISP.

α.15) Surface-active derivatives of montan, polyethylene and polypropylene waxes such as the Hoechst® waxes or the Licowet® brands by Clariant.

α.16) Surface-active phosphonates and phosphinates such as Fluowet®-PL by Clariant.

α.17) Poly- or perhalogenated surfactants such as, for example, Emulsogen®-1557 by Clariant.

The surfactants which are different from the surfactants b) and which are optionally present in the herbicidal compositions according to the invention are preferably of the type of the $C_8$–$C_{20}$-alkyl polyglycol ether sulfates, in particular $C_{10}$–$C_{18}$-alkyl polyglycol ether sulfates, which are preferably used in the form of their salts, for example alkali metal salts such as sodium salts or potassium salts, and/or ammonium salts, but also as alkaline earth metal salts such as magnesium salts, 2 to 5 ethylene oxide units preferably being present in the polyglycol moiety. An especially preferred example is sodium $C_{12}/C_{14}$-fatty alcohol diglycol ether sulfate (tradename for example Genapol ® LRO, Clariant GmbH).

Preferably, the herbicidal compositions according to the invention additionally comprise water and if appropriate, organic solvents besides components a), b) and c) and are formulated in the form of an aqueous concentrated dispersion or emulsion or as a tank mix in the form of a dilute dispersion, emulsion or solution with a degree of dilution of up to that of the ready-to-use spray mixture. A herbicidal composition prepared as a tank mix and comprising, for use, the preferred amounts of herbicide a), surfactant b) and humectant c) is especially preferred.

Mixtures or coformulations with other active substances such as, for example, insecticides, acaricides, herbicides, fungicides, safeners, fertilizers and/or growth regulators are also possible, if appropriate.

For use, concentrated formulations which are present in commercially available form are, if appropriate, diluted in the customary fashion, for example by means of water in the case of wettable powders, emulsifiable concentrates, dispersions and water-dispersible granules. Preparations in the form of dusts, spray granules, absorption granules, sprayable solutions and spray mixtures prepared as tank mix are not conventionally diluted further with additional inert substances prior to use. However, it may be advantageous or necessary to add further amounts of surfactants b), humectant c) and/or other conventional auxiliaries, in particular self-emulsifying oils or liquid paraffins, to the spray mixtures.

The application rate required of the herbicides a) varies with the external conditions such as temperature, humidity and the nature of the herbicide used. It can vary within wide limits, for example between 0.001 and 10 kg/ha or more of active substance, but it is preferably between 0.005 and 5 kg/ha.

The herbicidal compositions according to the invention have an outstanding herbicidal activity against a broad spectrum of economically important monocotyledonous and dicotyledonous harmful plants. The active ingredients also act efficiently on perennial weeds which produce shoots from rhizomes, rootstocks or other perennial organs and which are difficult to control. In this context, it does not matter whether the substances are applied before sowing, pre-emergence or post-emergence. Specific examples may be mentioned of some representatives of the monocotyledonous and dicotyledonous weed flora which can be controlled by the herbicidal compositions according to the invention, without the enumeration being a restriction to certain species.

Examples of weed species on which the herbicidal compositions act efficiently are, from amongst the monocotyledonous weed species, Avena, Lolium, Alopecurus, Phalaris, Echinochloa, Digitaria, Setaria and Bromus species, such as Bromus catharticus, Bromus secalinus, Bromus erectus, Bromus tectorum and Bromus japonicus, and Cyperus species from the annual group, and, among the perennial species, Agropyron, Cynodon, Imperata and Sorghum and also perennial Cyperus species.

In the case of the dicotyledonous weed species, the spectrum of action extends to genera such as, for example, Galium, Viola, Veronica, Lamium, Stellaria, Amaranthus, Sinapis, Ipomoea, Matricaria, Abutilon and Sida amongst the annuals, and Convolvulus, Cirsium, Rumex and Artemisia in the case of the perennial weeds.

The compositions according to the invention also act outstandingly efficiently on harmful plants which are found under the specific culture conditions in rice, such as, for example, Echinochloa, Sagittaria, Alisma, Eleocharis, Scirpus and Cyperus.

If the herbicidal compositions according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the herbicidal compositions according to the invention are applied post-emergence to the green parts of the plants, growth likewise stops drastically a very short time after the treatment, and the weed plants remain at the growth stage of the point of time of application, or they die completely after a certain time, so that in this manner competition by the weeds, which is harmful to the crop plants, is eliminated very early and in a sustained manner.

Even though the herbicidal compositions according to the invention have an outstanding herbicidal activity against monocotyledonous and dicotyledonous weeds, crop plants of economically important crops such as dicotyledonous crops such as, for example, soybeans, cotton, oilseed rape, sugarbeet, in particular soybeans, or graminaceous crops such as wheat, barley, rye, rice or maize, are harmed only to a minor extent, if at all. For these reasons, the present compounds are highly suitable for the selective control of undesired vegetation in stands of agriculturally useful plants or of ornamentals.

In addition, the herbicidal compositions according to the invention have outstanding growth-regulatory properties in crop plants. They engage in the plants' metabolism in a regulatory fashion and can thus be used for the directed control of plant constituents and for facilitating harvesting, such as, for example, by triggering desiccation and stunted growth. Moreover, they are also suitable for generally controlling and inhibiting undesired vegetative growth without destroying the plants in the process. Inhibition of the vegetative growth plays an important role in many monocotyledonous and dicotyledonous crops since lodging can be reduced, or prevented completely, thereby.

Owing to their herbicidal and plant-growth regulatory properties, the herbicidal compositions according to the invention can also be employed for controlling harmful plants in crops of genetically modified plants which are known or yet to be developed. As a rule, the transgenic plants are distinguished by particular advantageous properties, for example by resistances to certain pesticides, especially certain herbicides, resistances to plant diseases or to plant pathogens such as certain insects or microorganisms such as fungi, bacteria or viruses. Other particular properties concern for example the harvested material with regard to quantity, quality, storeability, composition and specific constituents. Thus, transgenic plants with an increased starch content or with a modified starch quality or with a different fatty acid composition of the harvested material are known.

The use of the compositions according to the invention in economically important transgenic crops of useful plants and ornamentals, such as of graminaceous crops such as wheat, barley, rye, oats, sorghum and millet, rice and maize or else crops of sugarbeet, cotton, soybean, oilseed rape, potatoes, tomatoes, peas and other vegetables is preferred. The compositions according to the invention may preferably be employed as herbicides in crops of useful plants which are resistant to the phytotoxic effects of the herbicides or which have been rendered resistant to the phytotoxic effects of the herbicides by recombinant means.

When the herbicidal compositions according to the invention are used in transgenic crops, effects are frequently observed—in addition to the effects on harmful plants which can be observed in other crops—which are specific for the application in the transgenic crop in question, for example a modified or specifically extended weed spectrum which can be controlled, altered application rates which can be employed for application, preferably good combining properties with the herbicides to which the transgenic crop is resistant, and an effect on growth and yield of the transgenic crop plants.

Subject of the invention is therefore also the use of the compositions according to the invention as herbicides for controlling harmful plants, preferably in crops of plants, it also being possible for the crops of plants to take the form of crops of transgenic plants.

The herbicidal compositions according to the invention can also be employed nonselectively for controlling undesired vegetation, for example in plantation crops, on verges, squares, industrial terrain or rail tracks.

Owing to the relatively low application rate of the herbicidal compositions according to the invention, they are generally already very well tolerated. In particular, a reduction in the absolute application rate is achieved by the combinations according to the invention, compared with the individual use of a herbicidal active substance.

Subject of the invention is thus also a method of controlling harmful plants, preferably for selectively controlling harmful plants in crops of useful plants, which comprises applying a herbicidally active amount of the abovementioned herbicides a) in combination with at least one of the surfactants b) and at least one humectant c), for example pre-emergence, post-emergence or pre- and post-emergence, preferably pre-emergence, jointly or in succession, to the plants, plant parts, plant seeds or the area on which the plants grow, for example the area under cultivation.

In a preferred method variant, the herbicides a) are applied in application rates of from 0.1 to 400 g of active substances/ha, preferably of from 0.5 to 200 g of active substance/ha. It is furthermore preferred to apply the active ingredients in the form of a readymix or in the form of tank mixes, where the individual components, for example in the form of formulations, are jointly mixed with water in the tank and the resulting spray mixture is applied.

Since the crop plant compatibility of the combinations according to the invention is extremely good, combined with a very high degree of control of the harmful plants, the combinations according to the invention can be considered as selective. In a preferred embodiment, herbicidal compositions with the active substance combinations according to the invention are therefore employed for selectively controlling undesired plants.

If, if desired, the compatibility and/or selectivity of the herbicidal compositions according to the invention is to be increased even further, it may be advantageous to apply them together with safeners or antidotes, either jointly in a mixture or staggered in time.

Compounds which are suitable as safeners or antidotes for the herbicidal compositions according to the invention are known, for example, from EP-A-333 131 (ZA-89/1960), EP-A-269 806 (U.S. Pat. No. 4,891,057), EP-A-346 620 (AU-A-89134951) and the international patent applications PCT/EP 90/01966 (WO-91108202) and PCTIEP 90102020 (WO-911078474) and literature cited therein or can be prepared by the processes described therein. Further suitable safeners are known from EP-A-94 349 (U.S. Pat. No. 4,902,304), EP-A-1 91 736 (U.S. Pat No 4,881,966) and EP-A-0 492 366 and the literature cited therein.

In a preferred embodiment, the herbicidal compositions of the present invention therefore comprise an additional content of one or more compounds which act as safeners or antidotes.

Especially preferred antidotes or safeners or groups of compounds which are suitable as safeners or antidotes for the above-described herbicidal compositions of the invention are, inter alia:

a) compounds of the dichlorophenylpyrazoline-3-carboxylic acid type, preferably compounds such as ethyl 1-(2,4-dichlorophenyl)-5-(ethoxycarbonyl)-5-methyl-2-pyrazoline-3-carboxylate (compound S1-1, mefenpyr-diethyl) and related compounds as are described in the international application WO 91/07874 (PCTIEP 90102020);

b) dichlorophenylpyrazolecarboxylic acid derivatives, preferably compounds such as ethyl 1-(2,4-dichlorophenyl)-

5-methylpyrazole-3-carboxylate (compound S1-2), ethyl 1-(2,4-dichlorophenyl)-5-isopropylpyrazole-3-carboxylate (compound S1-3), ethyl 1-(2,4-dichlorophenyl)-5-(1,1-dimethylethyl)pyrazole-3-carboxylate (compound S1-4), ethyl 1-(2,4-dichlorophenyl)-5-phenylpyrazole-3-carboxylate (compound S1-5) and related compounds as are described in EP-A-0 333 131 and EP-A-0 269 806;

c) compounds of the triazolecarboxylic acids type, preferably compounds such as ethyl 1-(2,4-dichlorophenyl)-5-trichloromethyl-(1H)-1,2,4-triazole-3-carboxylate (compound S1-6, fenchlorazole) and related compounds (see EP-A-0 174 562 and EP-A-0 346 620);

d) compounds of the dichlorobenzyl-2-isoxazoline-3-carboxylic acid type, compounds of the 5-benzyl- or 5-phenyl-2-isoxazoline-3-carboxylic acid type, preferably compounds such as ethyl 5-(2,4-dichlorobenzyl)-2-isoxazoline-3-carboxylate (compound S1-7) or ethyl 5-phenyl-2-isoxazoline-3-carboxylate (compound S1-8), and related compounds as are described in international patent application WO 91108202 (PCT/EP 90/01966);

e) compounds of the 8-quinolinoxyacetic acid type, preferably compounds such as 1-methylhex-1-yl (5-chloro-8-quinolinoxy)acetate (S2-1; cloquintocet-mexyl), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), ethyl 2-(2-propylideneiminooxy)-1-(5-chloro-8-quinolinoxy)acetate (S2-8), 2-oxoprop-1-yl (5-chloro-8-quinolinoxy)acetate (S2-9) and related compounds as are described in EP-A-0 086 750, EP-A-0 094 349 and EP-A-0 191 736 or EP-A-0 492 366;

f) compounds of the (5-chloro-8-quinolinoxy)malonic acid type, preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds as have been described and proposed in German patent application EP-A-0 582 198;

g) active substances of the type of the phenoxyacetic acid derivatives or phenoxypropionic acid derivatives or of the aromatic carboxylic acids such as, for example, 2,4-dichlorophenoxyacetic acid (and esters) (2,4-D), 4-chloro-2-methylphenoxypropionic acid (mecoprop), MCPA or 3,6-dichloro-2-methoxybenzoic acid (and esters) (dicamba).

h) compounds of the 5,5-diphenyl-2-isoxaoline-3-carboxylic acid type, preferably ethyl 5,5-diphenyl-2-isoxazoline-3-carboxylate (S3-1, isoxadifen-ethyl).

i) compounds which are known as safeners, for example for rice, such as fenclorim (=4,6-dichloro-2-phenylpyrimidine, Pesticide Manual, 11$^{th}$ Edition, 1997, pp. 511–512), dimepiperate (=S-1-methyl-1-phenylethyl piperidine-1-thiocarboxylate, Pesticide Manual, 11$^{th}$ Edition, 1997, pp. 404–405), daimuron (=1-(1-methyl-1-phenylethyl)-3-p-tolylurea, Pesticide Manual, 11$^{th}$ Edition, 1997, p. 330), cumyluron (=3-(2-chlorophenylmethyl)-1-(1-methyl-1-phenylethyl) urea, JP-A-60/087254), methoxyphenone (=3,3'-dimethyl-4-methoxybenzophenone, CSB (=1-bromo-4-(chloromethyl-sulfonyl)benzene, CAS-Reg. No. 54091–06–4).

In addition, at least some of the abovementioned compounds are described in EP-A-0 640 587, which is herewith referred to for disclosure purposes.

j) A further important group of compounds which are suitable as safeners and antidotes is known from WO 95107897.

The safeners (antidotes) of the above groups a) to j) reduce or prevent phytotoxic effects which may be observed when the herbicidal compositions according to the invention are employed in crops of useful plants, without adversely affecting the efficacy of the herbicides against harmful plants. This makes it possible considerably to widen the spectrum of application of the herbicidal compositions according to the invention; in particular, the use of safeners makes possible the application of herbicidal compositions which could previously only be employed to a limited extent or with insufficient success, i.e. of combinations which, at low dosages with a poor spectrum of action, led to insufficient control of the harmful plants without safener.

Components a), b) and c) of the herbicidal compositions according to the invention and the abovementioned safeners can be applied jointly (as readymix or by the tank mix method) or in succession in any desired sequence. The weight ratio safener:herbicide (compound(s) of the formula (I) and/or their salts) can vary within wide ranges and is preferably in the range of from 1:100 to 100:1, in particular of from 1:100 to 50:1. The amounts of herbicide(s) and safener(s) which are optimal in each case usually depend on the type of the herbicidal composition and/or on the safener used, and also on the nature of the plant stand to be treated.

Depending on their properties, the safeners can be used for pretreating the seed of the crop plant (seed dressing) or incorporated into the seed furrows prior to sowing or applied together with the herbicide mixture before or after emergence of the plants.

Pre-emergence treatment includes both the treatment of the area under cultivation before sowing and the treatment of the areas under cultivation where seed has been sown, but growth is as yet not present. The joint application with the herbicide mixture is preferred. Tank mixes or readymixes can be employed for this purpose.

The application rates required, of the safeners, can vary within wide limits, depending on the indication and the herbicide used; they are, as a rule, in the range of from 0.001 to 1 kg, preferably 0.005 to 0.2 kg, of active substance per hectare.

The herbicidal compositions according to the invention can be applied in the customary fashion, for example with water as carrier in spray mixture quantities of approximately 5 to 4000 liters/ha. Application of the compositions by what are known as the low-volume and ultra-low-volume methods (ULV) is also possible, as is their application in the form of granules and microgranules.

A preferred use relates to application of herbicidal compositions which contain components a), b) and c) in a synergistically active amount. The invention also extends to mixtures of one or more herbicides a) with one or more surfactants b) and one or more humectants c).

In addition, one, two or more agrochemical active substances other than herbicide a) (for example herbicides, insecticides, fungicides, safeners) may also be present in the herbicidal compositions of the invention for complementing the properties, usually in minor amounts.

This results in a large number of possibilities of combining several active substances with each other and of employing them jointly for controlling harmful plants in crops of plants without deviating from the spirit of the invention.

Thus, in a preferred embodiment, for example various active substances of the formula (I) may be combined with each other, for example mesosulfuron-methyl+iodosulfuron-methyl,
mesosulfuron-methyl+iodosulfuron-methyl-sodium,
mesosulfuron-methyl+foramsulfuron,
mesosulfuron-methyl+foramsulfuron-sodium,
mesosulfuron-methyl-sodium+iodosulfuron-methyl,
mesosulfuron-methyl-sodium+iodosulfuron-methyl-sodium,
mesosulfuron-methyl-sodium+foramsulfuron,
mesosulfuron-methyl-sodium+foramsulfuron-sodium,
foramsulfuron+iodosulfuron-methyl,
foramsulfuron+iodosulfuron-methyl-sodium,
foramsulfuron-sodium+iodosulfuron-methyl,
foramsulfuron-sodium +iodosulfuron-methyl-sodium.

The above-described active substance mixtures are preferably combined with a silicone surfactant such as Silwet® (Witco/Osi Corp.) as component b) and a lactic acid derivative such as sodium lactate as component c). In addition, preferably one or more safeners may be present, in particular the safeners mefenpyr-diethyl (S1-1), cloquintocet-mexyl (S2-1) and isoxadifen-ethyl (S3-1).

In conclusion, it can be said that the herbicidal compositions according to the invention have an outstanding herbicidal action and that in a preferred embodiment superadditive (=synergistic) effects are observed. In this case, the action in the combinations exceeds that of the individual components employed alone.

These effects make it possible inter alia to reduce the application rate, to control a broader spectrum of broad-leaved weeds and grass weeds, to fill in gaps of action, and permit a more rapid and more reliable action, a prolonged duration of action, complete control of the harmful plants with only one or few applications, and a widened period of application. The abovementioned properties are required in weed control practice in order to keep agricultural crops free from undesired plant competitors and thus to safeguard and/or increase the yields in terms of quality and quantity. The technical standard is exceeded markedly by the combinations according to the invention with regard to the properties described. Thus, a considerably improved reliability of action is observed under different environmental conditions.

The use examples which follow illustrate the invention and have no limiting character whatsoever.

EXAMPLES

Example 1
Preparation of the Spray Mixture

The individual components herbicide, surfactant and humectant as stated in Table 1 with regard to the application rates were added with stirring to a water application rate of 300 l/ha so that a homogeneous spray mixture was formed. The herbicide employed was mesosulfuron-methyl as 20 percent water-dispersible powder. The surfactant used was Silwet®L77 (Wacker) and the humectant used was sodium lactate as 50 percent aqueous solution (Merck KGaA, Darmstadt).

Example 2
Activity Against Grass Weeds

Seeds of the harmful plants AVEFA and LOLMU were sown in a sandy loam soil in round pots type 13 in a controlled-environment cabinet and watered slightly. During the entire experiment period, the substrate only received minimal irrigation. A daytime temperature of 18° C. and a night time temperature of 16° C. were adhered to, a uniform day length of 16 hours being achieved by additional illumination with sodium vapor lamps (approx. 7000 lux). The relative atmospheric humidity was 50%. Four weeks after sowing, the plants were treated on a laboratory spray conveyor with the spray mixture which had been prepared in accordance with Example 1. The water application rate for the spray application of the preparations was 300 l/ha. After the treatment, the plants were returned to the controlled-environment cabinet. Visual scoring was carried out 14 days after the application, using a percentage 20 scale of 0%=no damage to 100%=all plants dead. The results are shown in Table 1.

TABLE 1

| | | Damage in % | |
|---|---|---|---|
| Components | g a.i./ha | AVEFA | LOLMU |
| Mesosulfuron | 60 | 22 | 18 |
| Mesosulfuron + Silwet ® L77 | 60 50 | 32 | 36 |
| Mesosulfuron + Silwet ® L77 + sodium lactate | 60 50 150 | 68 | 60 |

| Abbreviations: | |
|---|---|
| g a.i./ha = | g of active ingredient/hectare |
| AVEFA = | Avena fatua |
| LOLMU = | Lolium multiflorum |
| Mesosulfuron = | mesosulfuron-methyl |

We claim:

1. A herbicidal composition comprising
   a) one or more herbicidal active substances from the group of the grass-controlling sulfonamides,
   b) one or more silicone surfactants, and
   c) one or more humectants.

2. A herbicidal composition as claimed in claim 1, comprising, as component a), a grass-controlling sulfonylurea.

3. A herbicidal composition as claimed claim 1, additionally comprising one or more further components from the group consisting of agrochemical active substances, additives conventionally used in the art of crop protection, and formulation auxiliaries.

4. The composition as claimed in claim 1, wherein the grass-controlling sulfonamide is selected from the group consisting of mesosulfuron-methyl, mesosulfuron-methyl sodium, iodosulfuron-methyl, iodosulfuron-methyl sodium, foramsulfuron, and foramsulfuron-sodium.

5. The composition as claimed in claim 1, wherein the grass-controlling sulfonamide is a compound of the formula

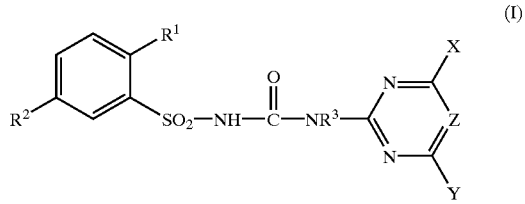

in which
R$^1$ is CO—R$^a$, in which R$^a$ is OH, C$_1$–C$_4$-alkoxy or NR$^b$R$^c$, in which R$^b$ and R$^c$ independently of one another are identical or different and are H or C$_1$–C$_4$-alkyl, $R^2$ is halogen or $(A)_n$—$NR^dR^e$ in which n is zero or 1, A is a group CR'R" in which R' and R" independently of one another are identical or different and are H or $C_1$–$C_4$-alkyl, $R^d$ is H or $C_1$–$C_4$-alkyl and $R^e$ is an acyl radical, $R^3$ is H or $C_1$–$C_4$-alkyl, X and Y independently of one another are identical or different and are $C_1$–$C_6$-alkyl, $C_1$–$C_6$-alkoxy or $C_1$–$C_6$-alkylthio, where each of the three above-mentioned radicals is unsubstituted or substituted by one or more radicals selected from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, and Z is CH or N.

6. The composition as claimed in claim 5, wherein the humectants is lactate.

7. A method for the preparation of a herbicidal composition defined as in claim 1, wherein components a), b) and c) are mixed.

8. The method as claimed in claim 7, wherein the components a), b) and c) are mixed by the tank mix method.

9. A method of controlling harmful plants, wherein the herbicidal composition defined as in claim 1 is applied pre-emergence, post-emergence or pre- and post-emergence to the plants, plant parts, plant seeds or the area on which the plants grow.

10. The method as claimed in claim 9, wherein the area on which the plants grow is an area under cultivation.

11. The method as claimed in claim 9, wherein the harmful plants are controlled selectively.

* * * * *